(12) United States Patent
Riesberg

(10) Patent No.: US 10,071,212 B1
(45) Date of Patent: Sep. 11, 2018

(54) ENDOTRACHEAL TUBE APPARATUS AND METHOD

(76) Inventor: Michael V. Riesberg, Pensacola, FL (US)

( * ) Notice: Subject to any disclaimer, the term of this patent is extended or adjusted under 35 U.S.C. 154(b) by 1060 days.

(21) Appl. No.: 13/199,396

(22) Filed: Aug. 29, 2011

(51) Int. Cl.
*A61M 16/00* (2006.01)

(52) U.S. Cl.
CPC .................................. *A61M 16/00* (2013.01)

(58) Field of Classification Search
CPC .............. A61M 16/04; A61M 16/0402; A61M 16/0434; A61M 16/044; A61M 16/0445; A61M 16/0454; A61M 16/0456; A61M 16/0459; A61M 16/0465; A61M 16/00; A61M 25/10; A61M 16/0427; A61M 16/0488
See application file for complete search history.

(56) References Cited

U.S. PATENT DOCUMENTS

| | | | | | |
|---|---|---|---|---|---|
| 3,625,793 | A | * | 12/1971 | Sheridan | A61M 25/001 156/229 |
| 3,774,616 | A | * | 11/1973 | White et al. | 128/200.26 |
| 4,498,473 | A | * | 2/1985 | Gereg | 128/207.15 |
| 5,642,730 | A | * | 7/1997 | Baran | 128/207.14 |
| 2009/0260632 | A1 | * | 10/2009 | Abnousi | A61M 16/04 128/207.15 |
| 2010/0288289 | A1 | * | 11/2010 | Nasir | A61M 16/04 128/861 |

* cited by examiner

*Primary Examiner* — Gregory Anderson
*Assistant Examiner* — Ned T Heffner
(74) *Attorney, Agent, or Firm* — J. Nevin Shaffer, Jr.

(57) ABSTRACT

An endotracheal tube apparatus and method includes a tube with a first end and a second end and an inside and an outside. Dual inflatable balloons are connected in spiral relation with the outside of the second end and a suction tube with more than one suction port is connected with the tube such that the more than one suction port captures secretions from the outside of the tube.

9 Claims, 3 Drawing Sheets

ENDOTRACHEAL TUBE APPARATUS AND METHOD

FIELD OF THE INVENTION

This invention relates to an endotracheal tube apparatus and method. In particular, in accordance with one embodiment, the invention relates to an endotracheal tube apparatus that includes a tube with a first end and a second end and an inside and an outside. Dual inflatable balloons are connected in spiral relation with the outside of the second end and a suction tube with more than one suction port is connected with the tube such that the more than one suction port captures secretions from the outside of the tube.

BACKGROUND OF THE INVENTION

Endotracheal intubation is one of the most commonly performed medical procedures in healthcare. The highest number of intubations occur in the surgical setting, with seventy percent of U.S. hospitals intubating an average of twenty patients per day in surgery cases lasting longer than one and a half hours. Seventy percent of U.S. hospitals also intubate three to five patients in non-surgical settings such as in ICUs and emergency rooms.

For over one hundred years, endotracheal intubation has been utilized to stabilize the airway and breathing for unconscious patients, anesthetized patients, or trauma patients. The basic design of prior art tubes consists of a pliable tube which can be inserted through the mouth or nose and into the trachea. To facilitate positive pressure into the lungs, most prior art endotracheal tubes include a single circumferential balloon at one end of the tube. When the balloon is inflated, it creates a pressure seal against the wall of the trachea to prevent air leak during ventilation.

Although the risks versus benefits of endotracheal intubation are weighted far to the advantage of the benefits side, Applicant has identified at least five primary problems with the prior art endotracheal tube design:

1. Accumulation of oropharyngeal secretions laden with bacteria. Studies show that the typical "head up" or "head flat" position in ICUs and operating rooms allow these oropharyngeal secretions to accumulate between the oral endotracheal tube and the wall of the trachea. This space that exists above the inflated endotracheal tube balloon and comprises the space between the endotracheal tube and the lumen of the trachea proper is what the Applicant refers to as the "mucus dead space". Secretions in the mucus dead space are inaccessible to independent oral suctioning or endo-lumen suctioning in ICU and surgery settings. With prior art tubes, with the balloon inflated, these secretions accumulate above the balloon. Further, when the prior art balloon is deflated, these secretions track downstream into the lungs. It is known that most aspiration pneumonias involve typical oral bacteria.

Although a "head down" position keeps secretions in the oral cavity, this position is often not optimal and can be compromising to neurosurgical and cardiac patients.

2. Trauma to the posterior larynx and upper esophagus. Typically, a prior art endotracheal tube fits and sits between both vocal cords and rests against the posterior larynx and esophageal opening. These tubes are typically constructed from a rigid plastic design in the areas of the tube that contact delicate vocal cord mucosa and cause pressure and adherent trauma that worsens an ulcer abrasion to the vocal cord mucosa. As a result, in many if not most cases a "granuloma" or pressure sore forms in this area, resulting in possible voice or swallowing complications. Pressure in this area can also result in a temporary vocal cord weakness or paralysis.

3. Circumferential pressure and ischemia against the wall of the trachea. The rounded form of the prior art endotracheal tube, coupled with constant pressure from a single balloon inflated for a prolonged period of time interrupts vital blood flow to the mucosa of the trachea and the underlying cartilage and can have a tourniquet effect. That is, constant occlusion of the blood supply can and does result in scar tissue formation below the vocal chords. This results in necrosis to the mucosa and flail segment to the underlying cartilage. This condition, known as "subglottic stenosis", is a very costly and complex condition to remedy and trachea narrowing below the vocal chords can result in severe impairment of breathing.

4. Constant balloon cuff pressure in a single/isolated region of the trachea. Constant pressure is often required for mechanical ventilation in ICU and surgical settings. The problem that often results from use of prior art tubes with the single inflatable balloon is a "flail segment" or a weakened cartilage wall of the trachea in the area of the inflated balloon. One prior art remedy to this serious problem is to simply move the balloon to a site below the flail segment. However, this practice often simply expands the area of injury to the trachea.

5. Accumulation of secretions below the balloon. The human muco-ciliary belt of the lining of the trachea tends to constantly drive lung secretions upwards toward the mouth. Prior art endotracheal tubes, with their single balloon cuff, stop the upward clearance of secretions at the balloon level. Although separate time consuming intra-luminal suctioning can recover some of these secretions, the constant pressure of the single balloon of the prior art can weaken or paralyze mucociliary clearance in a circumferential segment coincident with the area of balloon contact. Such compromise can increase the risk of aspiration and/or pneumonia.

In addition to these five major problems with prior art devices, Applicant has observed that a difficult dilemma often arises relating to how long a patient can remain intubated with prior art tubes before a surgical tracheotomy is required in order to avoid the above mentioned problems caused by the prior art tubes. Compared to successful extubation, tracheostomy involves more cost and risk. That is, tracheostomy also has potential complications of its own.

Certainly, if more patients can remain safely intubated for longer periods of time with fewer complications, the incidence and costs associated with surgical tracheostomy necessitated by the deficiencies of the prior art endotracheal tubes can be significantly reduced.

It, therefore, is an object of the invention to provide an improved endotracheal tube that addresses each of the above listed problems associated with prior art endotracheal tubes and that is practical and not excessively complicated.

SUMMARY OF THE INVENTION

Accordingly, an endotracheal tube apparatus of the present invention, according to one embodiment, includes a tube with a first end and a second end and an inside and an outside. Dual inflatable balloons are connected in spiral relation with the outside of the second end and a suction tube with more than one suction port is connected with the tube such that the more than one suction port captures secretions from the outside of the tube.

It should be understood that terms used herein are given their common meaning as known in the art. Thus, "tube" is known to mean a form that has an inside and an outside with an interior space created by the sides of the tube. Typically, the tube is cylindrical in shape but it may be any shape desired or found effectual for the circumstance.

"Spiral relation", as used herein, refers to a form created by an elongated wrapping of one item around another item. The stripes on a barber pole form a spiral in relation to the pole, for example only and not by way of limitation.

According to one aspect of this invention, the dual inflatable balloons include a first inflatable balloon and a second inflatable balloon connected in spiral relation with the second end of the tube and in such a manner that the first inflatable balloon is connected with the second end along a length of the tube above the second inflatable balloon. In one aspect, the first inflatable balloon is separately inflatable apart from the second inflatable balloon. In a further aspect, the suction tube includes two suction ports at the second end with one second end suction port at the first inflatable balloon and another second end suction port at the second inflatable balloon.

In another aspect of the invention, the suction tube includes an upper suction tube with an upper suction port connected at the first end of the tube where the upper suction port captures secretions from the outside of the tube at the first end of the tube.

In yet another aspect of this invention, an oral dam is provided that is connected with the first end of the tube on the outside of the tube. In one aspect, the oral dam is a retractable oral dam connected with a slidable sleeve such that movement of the slidable sleeve extends and retracts the oral dam.

In another aspect, a gel collar surrounds at least a segment of the outside of the tube. As used herein the term "gel" is used to identify a material that is not rigid but soft and yielding. A medical quality silicone is suitable such as that offered under the brand names Silflex and Mepifel, for example only and not by limitation. It is noted that in plastic surgery, surface application of such soft gels to a wound promotes healing and reduces scar tissue formation. Preferably, the gel collar of the present invention is applied to the length of the tube that would most likely be in surface contact with the vocal cord mucosa.

Finally, in one aspect, the invention includes dual inflatable balloons that are connected with an inflation tube such that the dual inflatable balloons are controllable to alternately inflate and deflate such that as one balloon is inflated the other balloon is deflated. That is, the balloons are manipulated such that a seal is maintained at all times as one balloon inflates and creates a seal while the other balloon deflates and releases the seal.

According to another embodiment of the invention, an endotracheal tube apparatus includes a tube with a first end and a second end and an inside and an outside. A first inflatable balloon is connected in spiral relation with the outside of the second end. A second inflatable balloon is connected in spiral relation with the outside of the second end as well. A first suction tube with a suction port is connected at the second end in relation with the first inflatable balloon where the suction port captures secretions from the outside of the tube. A second suction tube with a suction port is connected at the second end in relation with the second inflatable balloon where the suction port captures secretions from the outside of the tube. A first inflation tube is connected with the first inflatable balloon such that the first inflatable balloon is controllable to alternately inflate and deflate and a second inflation tube is connected with the second inflatable balloon such that the second inflatable balloon is controllable to alternately inflate and deflate.

As used herein, the term connected "in relation with" describes a connection in which one element is connected next to or in close proximity with another element. That is, there are no specific locations that are absolutely required for the required suction ports only that they be located in proximity to or relation with the listed elements.

In one aspect of this invention, the first inflatable balloon is connected with the second end above the second inflatable balloon. Again, as shown in the figures, here the two balloons are sequentially located along the tube one after the other. Obviously, it may be that other configurations are desired and useful too such as overlapping or entwined relationships.

In another aspect, an upper suction tube is provided with an upper suction port connected at the first end of the tube where the upper suction port captures secretions from the outside of the tube.

In one aspect, a retractable oral dam is connected with the first end of the tube on the outside of the tube. In a further aspect, the retractable oral dam is connected with a slidable sleeve such that movement of the slidable sleeve extends and retracts the oral dam.

In a further aspect, a gel collar is connected with the outside of the tube.

In a final aspect of this embodiment, the invention includes a monitor device. A pump device and a suction device are also provided and both are connected with the monitor device. Further, the pump device is connected with the first inflatable balloon and also the second inflatable balloon and the suction device is connected with the first suction tube and also the second suction tube.

As used herein the term "monitor device" is used to describe a device conformed to monitor and control the operation of the apparatus of the invention and control the timing and operation of the pump and suction devices as will be more fully described hereafter with regard to the figures. Suffice to say, any electro-mechanical devices now known or hereafter developed for monitoring, pumping and suctioning are included within the scope of the present invention. Such monitors, pumps and suction devices are well within the ability of those of ordinary skill in the art.

According to another embodiment of the invention, a method for using an endotracheal tube consists of the steps of:

a. providing a tube with a first end and a second end and an inside and an outside; with a first inflatable balloon connected in spiral relation with the outside of the second end; with a second inflatable balloon connected in spiral relation with the outside of the second end; with a first suction tube with a suction port connected at the second end in relation with the first inflatable balloon where the suction port captures secretions from the outside of the tube; with a second suction tube with a suction port connected at the second end in relation with the second inflatable balloon where the suction port captures secretions from the outside of the tube; with a first inflation tube connected with the first inflatable balloon such that the first inflatable balloon is controllable to alternately inflate and deflate; and with a second inflation tube connected with the second inflatable balloon such that the second inflatable balloon is controllable to alternately inflate and deflate; and b. connecting a pump device and a suction device with the tube such that the pump device is connected with the first inflatable balloon and also the second inflatable balloon and such that the suction device is connected with the first suction tube and also the second suction tube.

In another aspect, the method includes the step of connecting the pump device and the suction device to a monitor device.

In one aspect, the method includes connecting an upper suction tube with an upper suction port connected at the first end of the tube such that the upper suction port captures secretions from the outside of the tube at the first end of the tube.

In another aspect, the method includes providing a retractable oral dam connected with a slidable sleeve such that movement of the slidable sleeve extends and retracts the oral dam and where the slidable sleeve is connected with the first end on the outside of the tube.

DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF THE INVENTION

Figure 1:
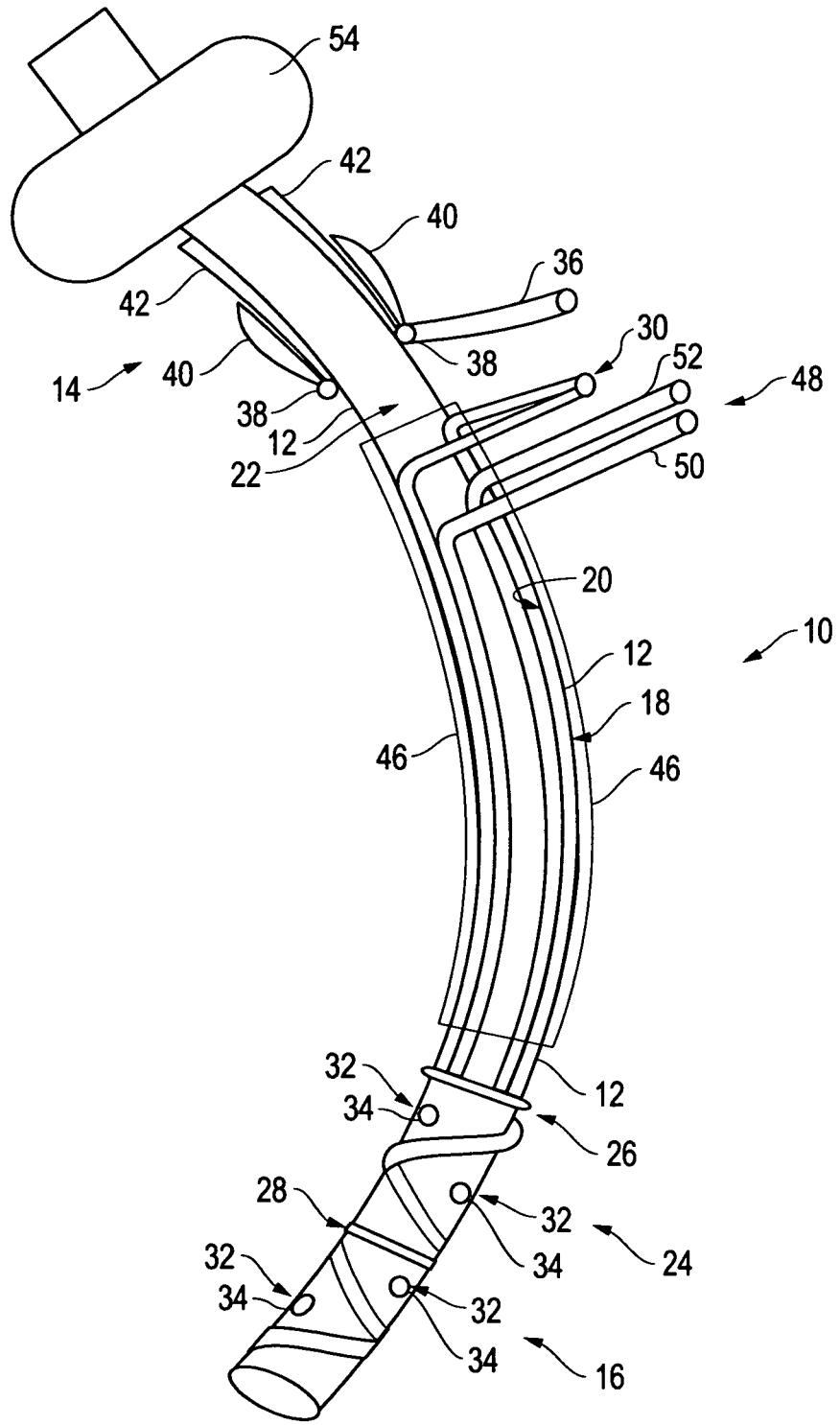
FIG. 1 is a side, partial section view of the endotracheal tube of the present invention with a retractable oral dam extended.
Figure 2:
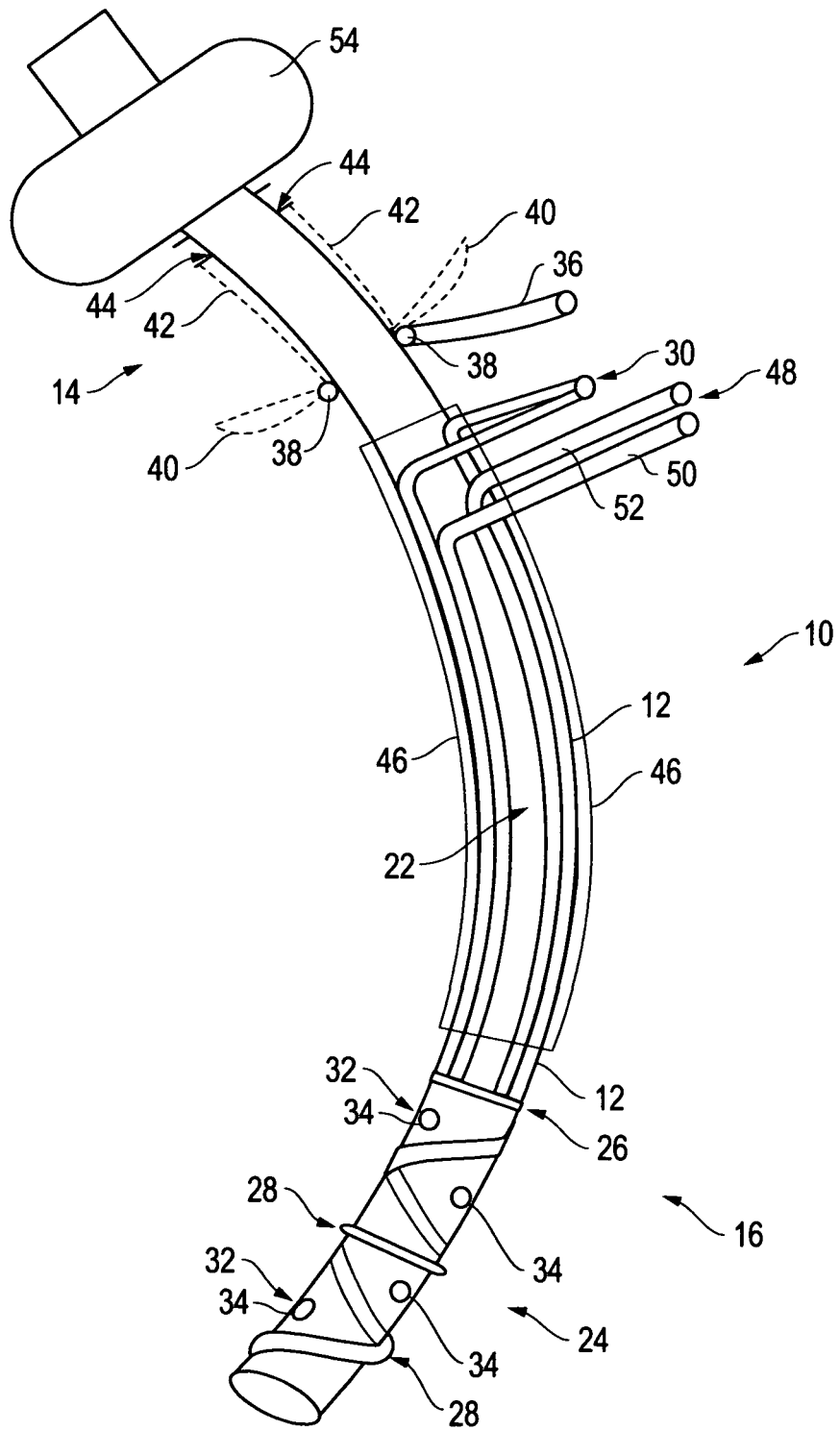
FIG. 2 is a side, partial section view of the invention of FIG. 1 with the retractable oral dam retracted.
Figure 3:
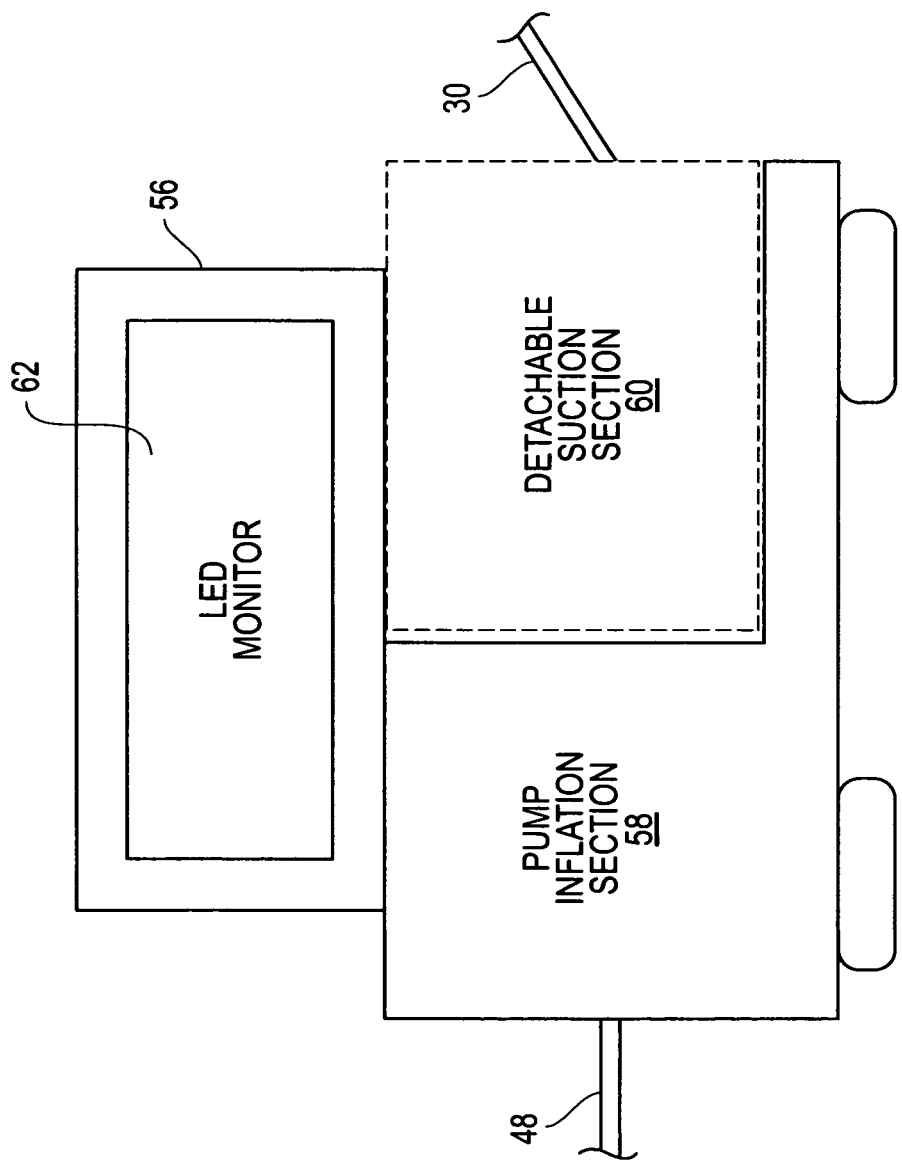
FIG. 3 is a schematic diagram of a monitor, a pump and a suction device according to one embodiment of the invention of FIG. 1.

The preferred embodiment of the present invention is illustrated by way of example in FIGS. 1-3. With specific reference to FIGS. 1 and 2, endotracheal tube apparatus 10 includes a tube 12. Tube 12 includes a first end 14 and a second end 16 and is formed of a pliable material such as plastic, for example only and not by way of limitation. The tube 12 has an exterior surface 18 and an interior surface 20. The tube 12 includes an empty interior space 22 created by those surfaces. Tube 12 may be cylindrically shaped as illustrated or any other useful form.

Preferably, the endotracheal tube apparatus 10 includes dual inflatable balloons 24 in the form of a first inflatable balloon 26 and a second inflatable balloon 28. As used herein, the term "inflatable" describes an object that is capable of holding a gas, such as air as with a hot air balloon, for example only and not by way of limitation. The term "balloon" is used to describe an object that is expandable but does not rupture upon ordinary use as with a common plastic or rubber balloon. Upon the release or relaxation of the incoming air, the balloon deflates to its resting size and upon the introduction of air it re-inflates. Thus, dual inflatable balloons 24 of the present invention may be inflated and deflated over and over again without failure. They may be constructed from any pliable and expandable material that returns to its original uninflated form upon the release of air such as a flexible, elastic plastic and rubber for example only.

Importantly, dual inflatable balloons 24 are connected in spiral relation with tube 12 and around tube 12 at the second end 16 of tube 12 as illustrated. In one embodiment, the first inflatable balloon 26 is connected to tube 12 above second inflatable balloon 28.

FIG. 1 illustrates this configuration and also shows the embodiment in which dual inflatable balloons 24 are separately and independently inflatable. FIG. 1 shows first inflatable balloon 26 inflated and extended away from the exterior surface 18 of tube 12 and second inflatable balloon 28 deflated. In this case, when the endotracheal tube 12 is in place in a patient, the expanded sides of inflatable balloon 26 contact the patient and seal endotracheal tube 12 against air leaks. Preferably in time with respiration of the patient, second inflatable balloon 28 inflates and then first inflatable seal 26 deflates as illustrated in FIG. 2. As a result, an ever changing contact is maintained with the patient without applying constant pressure at a single location and causing damage as described above.

Still referring to FIGS. 1 and 2, endotracheal tube apparatus 10 also includes, according to a preferred embodiment, a suction tube 30 with more than one suction port 32. The suction tube 30 is connected with tube 12 in any convenient manner. As shown in the figures, suction tube 30 starts on the outside of tube 12 and passes through the exterior surface 18 and into the interior space 22 of tube 12. The length of suction tube 30 then extends down the interior of tube 12 and ends at suction ports 32. That is, there is preferably more than one suction port 32 and, preferably, suction ports 32 capture secretions from the outside of tube 12. In one embodiment, suction tube 30 includes at least one second end suction port 34 at the first inflatable balloon 26 and at least one second end suction port 34 at the second inflatable balloon 28. Certainly there can be more suction ports 32 as desired.

Applicant has determined that there is a very advantageous effect that results from the spiral attachment of the inflatable balloons. An unexpected vortex or swirling of fluids is channeled into the space created by the pulsating inflatable balloons. This helps ensure that fluids are driven to the suction ports 32 and increases the effectiveness of the suctioning. That is the geometry of the spiral shape of the balloons spins the airflow between the tube 12 and the trachea and, applicant has found, separates solid mucous very effectively so as to be easily captured at the suction ports 32. Additionally, the spiral shape of the dual balloons 24 minimizes balloon contact area with the mucosa of the trachea.

FIGS. 1 and 2 also illustrate another aspect of the invention in the form of an upper suction tube 36 with at least one upper suction port 38 connected at the first end 14 of the tube 12 such that the at least one upper suction port 38 captures secretions from the outside of the tube 12 at the first end 14 of the tube 12.

Still further, FIGS. 1 and 2 illustrate another aspect of the invention, an oral dam 40 connected with the first end 14 on the outside of tube 12. Oral dam 40 is shown in FIG. 1 in a "raised" or "retracted" position and in FIG. 2 in a "lowered" or "extended" position (shown in dotted lines). Preferably, oral dam 40 is a retractable oral dam as shown although a fixed oral dam 40 may be desired.

A retractable oral dam 40 is provided by connecting it with a slidable sleeve 42 such that movement of slidable sleeve 42 extends and retracts the oral dam 40. In FIG. 1, slidable sleeve 42 is at its upper limit near the top of the first end 14 of tube 12. Slidable sleeve 42 fits over the exterior surface 18 as shown and slides up and down the exterior surface 18 when moved.

Oral dam 40 is hingedly connected with slidable sleeve 42 such that movement of the slidable sleeve 42 to the upper limit shown in FIG. 1, causes the hinged oral dam 40 to retract and fold against the sides of the slidable sleeve 42 thus allowing a clear view and unobstructed access to the tube 14 below the oral dam 40 when needed.

When it is desired to extend oral dam 40, as shown in FIG. 2, slidable sleeve 42 is moved down the exterior surface 18 of tube 12 in the direction of second end 16. Again, the hinged connection and movement of the slidable sleeve results in the extension of oral dam 40 as shown in FIG. 2. A lock notch 44 may be provided at then end of the farthest desired travel of slidable sleeve 42 to hold slidable sleeve 42 and oral dam 40 in the extended position shown in FIG. 2.

FIGS. 1 and 2 also illustrate a gel collar 46. Gel collar 46 surrounds at least a segment or part of the exterior surface 18 of tube 12. As illustrated, gel collar 46 is shown connected with tube 12 below the oral dam 40 at first end 14 and above the dual inflatable balloons 24 at the second end 16 of tube 12. Applicant has found that the gel collar 46 may be applied to approximately five centimeters of the tube 12 that are most likely to be in surface contact with the focal cord mucosa. Certainly, more or less of tube 12 may be covered with gel collar 46 as desired.

Gel collar 46 is required to be softer than tube 12. That is tube 12 may be pliable but must be rigid enough to enable insertion and withdrawal of the tube 12 in use. As discussed above, prior art tubes even though pliable still can cause considerable harm. Thus, the function of gel collar 46 is to provide a more pliable softer contact surface. Gel collar 46 may be made of any soft, pliable, yet sturdy, material such as medical quality silicone or any other such material now known or hereafter developed.

Preferably, endotracheal tube apparatus 10 also includes an inflation tube 48 such that the dual inflatable balloons 24 are controllable to alternately inflate and deflate such that as one balloon is inflated the other balloon is deflated as discussed above. Thus, preferably, there is a first inflation tube 50 and a second inflation tube 52. The first inflation tube 50 is connected with the first inflatable balloon 26 and the second inflation tube 52 is connected with the second inflatable balloon 28.

FIGS. 1 and 2 also show a stop 54 at the first end 14 that prevents the insertion of tube 12 beyond the extended stop 54.

Referring now to FIG. 3, other features of the invention are discussed. In a preferred embodiment, a monitor device 56 is provided and a pump device 58 and a suction device 60 are both connected with the monitor device 56. Pump device 58 is connected with the dual inflatable balloons 24, first inflatable balloon 26 and second inflatable balloon 28, and suction device 60 is connected with suction tube 30 as a first suction tube connection and with upper suction tube 36 as a second suction tube connection. Pump device 58 pumps air, for example only, when activated to inflate the inflatable balloons. When not pumping air, air is free to escape from pump device 58. It may also be that pump device 58 may be reversed to actively evacuate or suck air from a particular balloon to assist with deflation.

Suction device 60 applies a suction to draw fluids into the suction tubes and provides a container for collection of extracted fluids. Suction device 60 may be detachable from the assembly shown in FIG. 3 to allow easy disposal of fluids and cleaning.

Monitor device 56 is an electronic monitor as is known in the art, such as a computer. As such monitor device 56 is connected with and controls the operation of pump device 58 and suction device 60. An LED screen 62 in monitor device 56 is provided for observing the function of the devices as desired.

By way of continued explanation, Applicant's endotracheal tube apparatus 10 addresses all of the problems set forth herein with regard to prior art tubes and is an efficient and not overly complex improvement on them. In use, once the tube 14 is inserted, slidable sleeve 42 is operated to extend oral dam 40. This creates a collection point for the collection of oropharyngeal secretions. Again, it is known that oropharyngeal bacteria result in biofilm formation. With gravity drawing these secretions toward the trachea and the lungs, there is a risk of aspiration pneumonia, trachemalacia, and subglottic stenosis. Slidable sleeve 42, when advanced inferiorly toward the second end 16, opens upper suction tube 36 and upper suction ports 38. If tube 14 repositioning is necessary, drawing the slidable sleeve 42 toward the proximal, first, end 14 and collapses the oral dam 40 for better visibility.

Further, as mentioned, pressure trauma to the posterior larynx is a problem with prior art devices. When the prior art pliable but rigid tubes rests against the vocal cords and posterior glottis, granuloma formation can result. Thus, gel collar 46 is provided as a soft pliable layer that surrounds tube 12 and produces a cushioning effect at the contact points of the vocal cords and opening of the esophagus. The gel collar 46 may be made of slippery, lubricating material or include a layer of lubricating material such as medical grade silicone to minimize friction with these sensitive areas.

Circumferential pressure against the wall of the trachea is an inescapable fact of prior art endotracheal tubes. The result, again, is ischemia to a long and circumferential segment of trachea mucosa. To overcome this problem, Applicant's dual inflatable balloon design has a spiral configuration. The spiral design minimizes surface contact while at the same time providing a cuff seal for positive pressure ventilation. The spiral design prevents a circumferential ischemia from causing a narrow segment of granulation tissue. The spiral design also prevents circumferential flail segment of the trachea.

Still further, the spiral design creates channel that enable the application of vortex suction. Applicant has found this provides a much more effective suction result.

Additionally, by alternating inflation and deflation of the dual inflatable balloons 24, preferably timed with the inspiration/expiration of the respiratory cycle, the pressure of the cuff inflation is alternated with relief of pressure. As a result, ischemia of the trachea mucosa is minimized. By alternating inflation and deflation between the two balloons 24 by means of monitor device 56 in this manner, a cuff seal is maintained at all times for positive pressure ventilation. The alternating inflation and deflation is accomplished, according to one embodiment, by attachment of the suction and inflation tubes with the suction device 60 and the pump device 58 and controlled by monitor device 56. Timing of inflations cycles can be set, for example only, on the monitor device 56 by using a "mode" button to display "Set Balloon Inflation Timing", "Set Balloon Inflation Pressure", "Set Suction Pressure", "Purge Suction Tubing", for example only. Buttons can be used to set seconds/minutes on inflation timing, pressure in cm H20 and the like. Further, suction could operate from a standard hospital wall suction system or a small fan utilizing turbine fan blade technology (similar to a jet engine or vortex vacuum cleaner) can be mounted on the base of the device that can either be a suction booster or an independent suction apparatus, again for example only.

Moreover, the accumulation of secretions and biofilm between the tube 12 and the wall of the trachea is prevented by means of vortex suction at the location of the dual inflatable balloons 24. When each spiral balloon inflates, it helps drive the secretions within the channels formed by the balloon. The shape of the suction channels is a cyclone or vortex. In a conventional prior art balloon endotracheal cuff, the mucociliary belt that clears tracheal mucous in an uphill direction is stopped at the level of the balloon cuff. After the prior art balloon cuff has been inflated for a prolonged period of time, the mucociliary belt becomes weakened or even paralyzed even after cuff deflation. Impairment of the mucociliary clearance increases the risk of aspiration pneumonia associated with tracheal intubations. In Applicant's invention, suction ports 32 and 38 at the first inflatable balloon 26 and the second inflatable balloon 28 capture and deliver the secretions to suction tubes 30 and 36 for collection at suction device 60. Again, Applicant has identified a "mucous dead space" that exists above the balloon between the wall of the tube and the wall of the trachea. Mucous that accumulates here is inaccessible to manual suctioning of the oral cavity, oropharynx, or the subglottis.

Other elements of the present invention include the tubing connecting tube 14 with the pump and suction devices 60 and 62.

The connection tubing may be in any configuration but Applicant believes a preferred embodiment is four tubes. Tube one collects oropharyngeal secretions as illustrated by upper suction tube 36 in the Figures. Tube two collects secretions from the areas near first inflatable balloon 26 and second inflatable balloon 28 by suction tube 30 which combines the two separate suctions into one. Tube three connects with first inflation tube 50 for inflation/deflation of the first inflatable balloon 26. And tube four connects with second inflation tube 52 for inflation/deflation of the second inflatable balloon 28.

Again, preferably, the four separate tubing sections converge into a single point hub connector. This hub connector (not shown) is asymmetric so that the proper tubing lines up with the proper corresponding extension tubing for connection with the proper device, pump or suction. It is anticipated that the extension tubing, the four separate tubing sections (two for suction and two for pumping air) are integrated into a single tube. At the opposite end, the extension tubing diverges into two main sections (one section contains the two suction tubes and the other section contains the two pump tubes). The two pump tubes diverge, for example, into Port A and Port B on the pump device 58 and connect accordingly for alternating inflation and deflation of dual inflatable balloons 24 as described above.

The two suction tubes diverge, for example, into Part A and Port B and connect with the suction device 60 accordingly. Again, Applicant anticipates that the connection ports will be configured so that the Pump ports can not be connected to the Suction ports erroneously.

Other aspects of the invention include use of disposable elements that come in contact with the patient and secretions, such as the tube and tubing, for example. Other elements, the monitor, pump and suction devices are designed to be portable and reusable. The monitor device uses any programmable device such as a micro chip to control the operation of the pump and suction device. The LED screen displays appropriate messages and alerts, timing of inflation and deflation, suction pressures, balloon pressures and the like. As is known in the art, setting the pressures and sensing and adjusting them as set is a proper function of the monitor. Sensors in the suction section enable the monitor to adjust pressures to the selected settings. Alerts displayed include, for example only, "first balloon malfunction", "second balloon malfunction", "upper suction malfunction", "battery low", and "lower suction malfunction".

The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:

1. An endotracheal tube apparatus for insertion in a trachea, the apparatus comprising:
   a. a tube with a first end and a second end and an inside and an outside;
   b. dual inflatable balloons one after the other without overlapping connection with each other connected in spiral relation on the outside of said second end such that each of the dual inflatable balloons wraps around said tube in at least one complete spiral forming a suction channel on the outside of said tube and wherein each of the dual inflatable balloons is configured to circumferentially contact the trachea to form a complete cuff seal against the trachea when inserted and inflated; and
   c. a suction tube with more than one suction port in said outside of said tube such that said more than one suction port captures secretions from the outside of said tube from within said suction channel.

2. The apparatus of claim 1 wherein the dual inflatable balloons include a first inflatable balloon and a second inflatable balloon connected in spiral relation with said second end of said tube wherein said first inflatable balloon is connected with said second end above said second inflatable balloon.

3. The apparatus of claim 1 wherein said suction tube includes an upper suction tube with at least one upper suction port in said outside of said first end of said tube wherein said at least one upper suction port captures secretions from the outside of said tube at said first end of said tube.

4. The apparatus of claim 1 further including a stop at the first end preventing insertion of said tube beyond said stop and an oral dam connected with said first end on the outside of said tube below said stop wherein said oral dam collects secretions.

5. The apparatus of claim 4 wherein said oral dam is a retractable oral dam connected with a slidable sleeve such that movement of said slidable sleeve extends and retracts said oral dam.

6. The apparatus of claim 1 further including a gel collar surrounding at least a segment of said outside of said tube.

7. The apparatus of claim 1 wherein said dual inflatable balloons are connected with an inflation tube such that said dual inflatable balloons are controllable to alternately inflate and deflate such that as one balloon is inflated another balloon is deflated.

8. The apparatus of claim 2 wherein said suction tube includes at least two suction ports at said second end with at least one second end suction port at said first inflatable balloon in said suction channel of said first inflatable balloon and at least one second end suction port at said second inflatable balloon in said suction channel of aid second inflatable balloon.

9. The apparatus of claim 2 wherein said first inflatable balloon is separately inflatable apart from said second inflatable balloon.

* * * * *